(12) United States Patent
Suzuki et al.

(10) Patent No.: US 10,064,979 B2
(45) Date of Patent: Sep. 4, 2018

(54) BONE REGENERATION MATERIAL

(71) Applicant: TOHOKU UNIVERSITY, Miyagi (JP)

(72) Inventors: Osamu Suzuki, Miyagi (JP); Keiichi Sasaki, Miyagi (JP); Takahisa Anada, Miyagi (JP); Risa Ishiko-Uzuka, Miyagi (JP)

(73) Assignee: TOHOKU UNIVERSITY, Miyagi (JP)

( * ) Notice: Subject to any disclaimer, the term of this patent is extended or adjusted under 35 U.S.C. 154(b) by 30 days.

(21) Appl. No.: 15/039,480

(22) PCT Filed: Dec. 1, 2014

(86) PCT No.: PCT/JP2014/081770
§ 371 (c)(1),
(2) Date: Nov. 14, 2016

(87) PCT Pub. No.: WO2015/083668
PCT Pub. Date: Jun. 11, 2015

(65) Prior Publication Data
US 2017/0049933 A1    Feb. 23, 2017

(30) Foreign Application Priority Data
Dec. 2, 2013   (JP) .................................. 2013-249675

(51) Int. Cl.
*A61L 27/46* (2006.01)
*A61L 27/12* (2006.01)
*A61L 27/22* (2006.01)

(52) U.S. Cl.
CPC .............. *A61L 27/46* (2013.01); *A61L 27/12* (2013.01); *A61L 27/222* (2013.01); *A61L 2430/02* (2013.01)

(58) Field of Classification Search
CPC ........ A61L 27/46; A61L 27/12; A61L 27/222; A61L 2430/02
See application file for complete search history.

(56) References Cited

FOREIGN PATENT DOCUMENTS

| JP | 2006-167445 | 6/2006 |
|---|---|---|
| JP | 2007-031226 | 2/2007 |
| JP | 2010-110404 | 5/2010 |
| JP | 2011-234799 | 11/2011 |
| JP | 2013-106644 | 6/2013 |
| JP | 2013106644 A * | 6/2013 ............. A61L 27/00 |

OTHER PUBLICATIONS

Suzuki et al., *Maclura pomifera* agglutinin-binding glycoconjugates on converted apatite from synthetic octacalcium phosphate implanted into subperiosteal region of mouse calvaria, Bone and Mineral, vol. 20, 1993, pp. 151-166.
Suzuki et al., Bone Formation on Synthetic Precursors of Hydroxyapatite, Tohoku J. Exp. Med., vol. 164, 1991, pp. 37-50.
Miura et al., Characterization and bioactivity of nano-submicro octacalcium phosphate/gelatin composite, Applied Surface Science, vol. 282, 2013, pp. 138-145.
Handa et al., The effect of an octacalcium phosphate co-precipitated gelatin composite on the repair of critical-sized rat calvarial defects, Acta Biomaterialia, vol. 5, 2012, pp. 1190-1200.
Murakami et al., Comparative study on bone regeneration by synthetic octacalcium phosphate with various granule sizes, Acta Biomaterialia, vol. 6, No. 4, 2010, pp. 1542-1548.
International Search Report dated Mar. 10, 2015 in corresponding International Application No. PCT/JP2014/081770.
International Preliminary Report on Patentability dated Sep. 9, 2015 in corresponding International Application No. PCT/JP2014/081770.

\* cited by examiner

*Primary Examiner* — Michael B. Pallay
(74) *Attorney, Agent, or Firm* — Wenderoth, Lind & Ponack, L.L.P.

(57) ABSTRACT

A method for producing a bone regeneration material containing an octacalcium phosphate-gelatin complex, the method including: co-precipitating octacalcium phosphate with gelatin to produce an octacalcium phosphate-gelatin co-precipitate; washing the co-precipitate with a washing liquid to remove gelatin from the co-precipitate, thereby obtaining an octacalcium phosphate slurry; dispersing the octacalcium phosphate slurry or dry granules formed using the slurry in an aqueous gelatin solution; and drying the dispersion of octacalcium phosphate dispersed in the aqueous gelatin solution to produce an octacalcium phosphate-gelatin complex.

8 Claims, 2 Drawing Sheets
(2 of 2 Drawing Sheet(s) Filed in Color)

BONE REGENERATION MATERIAL

CROSS-REFERENCE TO RELATED APPLICATION

This application claims priority to Japan Patent Application No. 2013-249675, filed on Dec. 2, 2013 (the disclosure of which is incorporated herein by reference in its entirety).

TECHNICAL FIELD

The present invention relates to a method for producing a bone regeneration material and a bone regeneration material produced by the method.

BACKGROUND ART

Octacalcium phosphate ($Ca_8H_2(PO_4)_6 \cdot 5H_2O$, hereinafter sometimes referred to as "OCP"), which is a precursor of hydroxyapatite, has come into use as a synthetic bone material. To improve its moldability, OCP is usually used in the form of a complex with a polymeric material, such as alginic acid, gelatin (hereinafter sometimes referred to as "Gel"), or collagen. As bone regeneration materials comprising such a complex, for example, Patent Literature (PTL) 1 discloses a bone regeneration material comprising a dehydrothermally crosslinked co-precipitate of OCP and gelatin, and Patent Literature (PTL) 2 discloses a bone regeneration material comprising a complex of an OCP fine powder and gelatin.

CITATION LIST

Patent Literature

PTL 1: JP2011-234799A
PTL 2: JP2013-106644A

SUMMARY OF INVENTION

Technical Problem

However, conventional bone regeneration materials comprising a complex of octacalcium phosphate and gelatin have problems; for example, the concentration of OCP in the final complex is limited by the concentration of a gelatin solution, and the obtained bone regeneration material is difficult to handle.

An object of the present invention is to provide a bone regeneration material with high bone regeneration capacity, the bone regeneration material having such an elastic modulus as to be easily handled and/or containing a high concentration of OCP.

Solution to Problem

To achieve the above object, the present inventors conducted further extensive research on methods for producing a bone regeneration material comprising a complex of OCP and gelatin using a co-precipitation method and a wet method. The inventors found that a complex of OCP and gelatin produced under specific conditions has unexpectedly high bone generation capacity and can particularly produce a good-quality regenerated bone. The present invention has been accomplished based on this finding.

According to a first aspect of the invention, there is provided a method for producing a bone regeneration material comprising a complex of octacalcium phosphate and gelatin, the method comprising: co-precipitating octacalcium phosphate with gelatin to produce a co-precipitate of octacalcium phosphate and gelatin; washing the co-precipitate with a washing liquid to remove gelatin from the co-precipitate, thus producing a slurry of octacalcium phosphate; dispersing either the octacalcium phosphate slurry or dry granules formed using the slurry in an aqueous gelatin solution; and drying the dispersion of octacalcium phosphate dispersed in the aqueous gelatin solution to obtain a complex of octacalcium phosphate and gelatin.

In one embodiment of the present invention, the complex of octacalcium phosphate and gelatin contains octacalcium phosphate in an amount of more than 40 mass % but not more than 90 mass % and gelatin in an amount of at least 10 mass % and less than 60 mass %, based on the mass of the complex.

In another embodiment of the present invention, there is provided a bone regeneration material produced by the above method, the complex of octacalcium phosphate and gelatin containing octacalcium phosphate in an amount of 10 mass % to 90 mass %, based on the mass of the complex.

According to a second aspect of the present invention, there is provided a method for producing a bone regeneration material comprising a complex of octacalcium phosphate and gelatin, the method comprising: dispersing octacalcium phosphate granules with a particle size of 10 to 1,000 μm in an aqueous gelatin solution; and drying the dispersion of octacalcium phosphate granules dispersed in the aqueous gelatin solution to produce a complex of octacalcium phosphate and gelatin, the complex containing octacalcium phosphate in an amount of 10 mass % to 90 mass %, based on the mass of the complex, the proportion of octacalcium phosphate to gelatin being 0.1 to 9 parts by mass of octacalcium phosphate per part by mass of gelatin.

In one embodiment of the present invention, the octacalcium phosphate granules to be dispersed in the aqueous gelatin solution have a particle size of 300 to 500 μm.

In another embodiment of the present invention, the complex has an elastic modulus of 0.4 MPa or more.

According to a third aspect of the present invention, there is provided a bone regeneration material comprising a complex of octacalcium phosphate and gelatin, the complex containing octacalcium phosphate in an amount of 20 mass % to 90 mass %, based on the mass of the complex, the octacalcium phosphate in the complex having a particle size of 300 to 500 μm, and the proportion of octacalcium phosphate to gelatin being 0.1 to 9 parts by mass of octacalcium phosphate, per part by mass of gelatin.

Advantageous Effects of Invention

According to the present invention, there is provided a bone regeneration material with excellent bone regeneration capacity, the bone regeneration material containing a high concentration of OCP and/or being easy to handle.

BRIEF DESCRIPTION OF DRAWINGS

The patent or application file contains at least one drawing executed in color. Copies of this patent or patent application publication with color drawings will be provided by the Office upon request and payment of the necessary fee.

DESCRIPTION OF EMBODIMENTS

Figure 1:
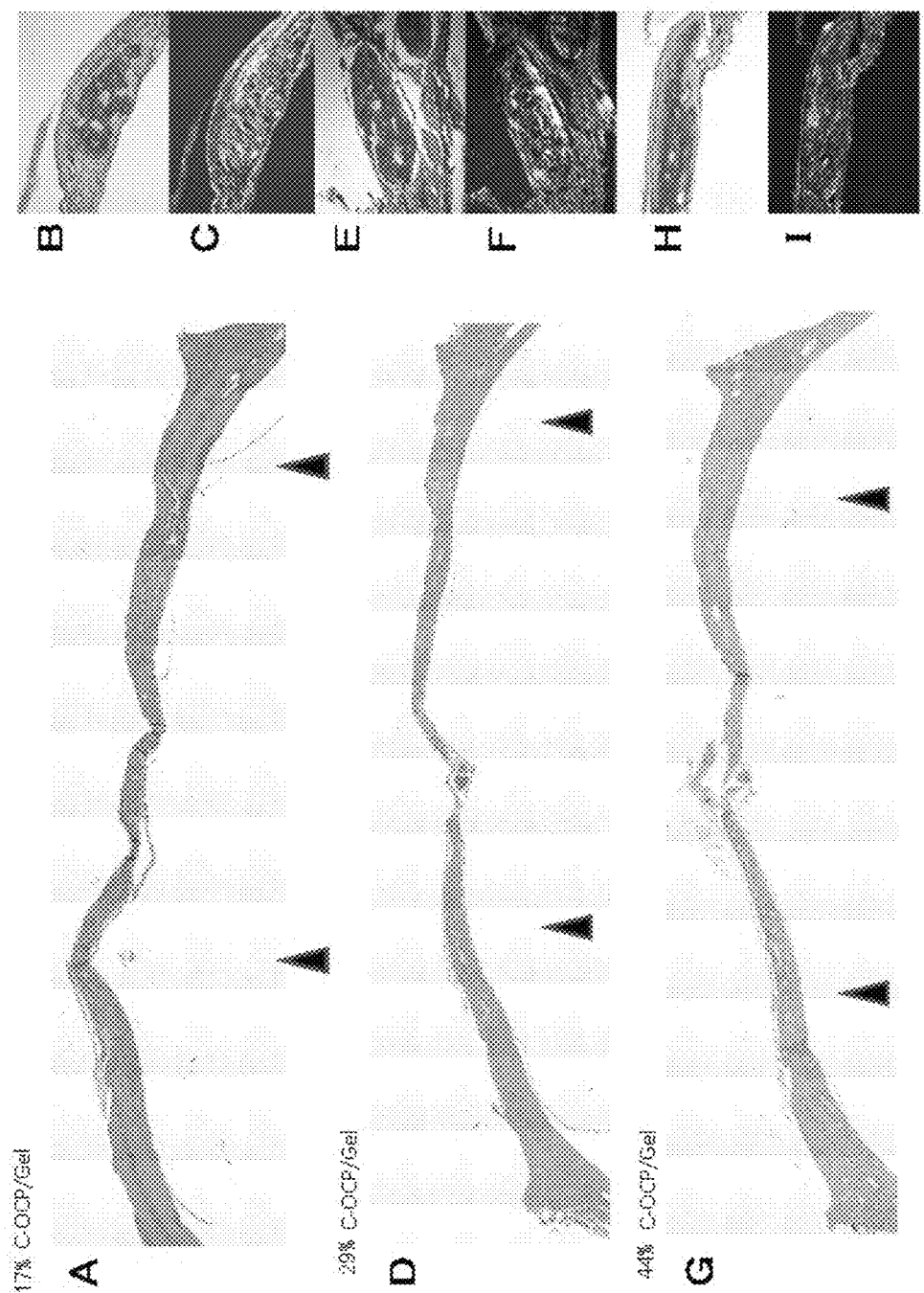
FIG. 1 shows photographs (A, D, G) of hematoxylin and eosin (HE) staining showing the cross sections of regenerated skulls in rats 8 weeks after each OCP/Gel disk produced by a co-precipitation method was implanted into a bone defect in the skull (wherein black triangles indicate the sites of defects created); bright-field photographs (B, E, H) of Sirius red staining; and polarized light photographs (C, F, I); A to C: OCP/Gel (17/83) disks, D to F: OCP/Gel (29/71) disks, and G to I: OCP/Gel (44/56) disks.

The use of the terms "a," "an," and "the" in this specification is to be construed to cover both their singular and plural meanings, unless otherwise indicated herein or clearly contradicted by context.

The present invention provides a method of producing a bone regeneration material comprising a complex of octacalcium phosphate and gelatin (hereinafter also referred to as an "OCP/Gel complex").

1. Preparation of OCP by Co-Precipitation

In one aspect of the method of the present invention, octacalcium phosphate (OCP) is prepared by a co-precipitation method. First, OCP and gelatin are co-precipitated to form an OCP/Gel complex. The OCP/Gel complex is obtained, for example, by using a method comprising adding an aqueous calcium solution dropwise to or injecting an aqueous calcium solution into an aqueous solution containing gelatin and phosphoric acid, or a method comprising adding an aqueous phosphoric acid solution dropwise to or injecting an aqueous phosphoric acid solution into an aqueous solution containing gelatin and calcium.

With respect to the method for co-precipitating OCP and gelatin, please refer to Handa T. et al., Acta Biomater 2012; 8: 1190-1200 or JP2011-234799A.

The gelatin to be used is not particularly limited. Gelatin is usually obtained by heat-treating collagen. Commercially available gelatins can also be used. The collagen to be used is not particularly limited. Examples of collagens include collagens derived from porcine or bovine skin, bones, or tendons. Commercially available collagens can also be used.

The phosphoric acid to be used is not particularly limited as long as it is a compound that produces $PO_4^{3-}$ in an aqueous solution. Examples of such compounds include disodium hydrogen phosphate, ammonium phosphate, and orthophosphoric acid.

The calcium to be used is not particularly limited as long as it is a compound that produces $Ca^{2+}$ in an aqueous solution. Examples of such compounds include calcium acetate, calcium chloride, and calcium nitrate.

The proportion of phosphoric acid to calcium is not particularly limited. Preferably, the molar ratio of phosphoric acid to calcium is 0.71:1 to 1.10:1, and more preferably 0.73:1 to 1.00:1.

The aqueous solution containing gelatin and phosphoric acid and the aqueous solution containing gelatin and calcium preferably have a pH of 4.5 to 7.5. The solution may contain a buffer component so that mixing an aqueous calcium solution or an aqueous phosphoric acid solution does not change the pH.

The dropwise addition or injection of an aqueous calcium solution into an aqueous solution containing gelatin and phosphoric acid, or the dropwise addition or injection of an aqueous phosphoric acid solution into an aqueous solution containing gelatin and calcium is preferably performed at 50° C. to 80° C., and more preferably at about 60° C. to 75° C. When the temperature is lower than 50° C. or higher than 80° C., OCP is hard to produce.

"Dropwise addition" or "adding . . . dropwise" as used herein refers to the addition of droplets of one solution to another solution. "Injection" or "injecting" as used herein refers to the addition of one solution to another solution using a hollow tube, such as a tube.

Next, the OCP/Gel complex obtained by using a co-precipitation method is washed with a washing liquid to remove gelatin, thus producing a slurry of OCP. The washing liquid may be pure water or may contain a buffer component, phosphate ions, calcium ions, etc. Pure water is preferable. The washing may be performed once or several times. Removing gelatin once enables the adjustment of the concentrations of OCP and gelatin in the OCP/Gel complex. This slurry of OCP is added to an aqueous gelatin solution as described below to obtain an OCP/Gel complex of the present invention.

The slurry of OCP may be heat-treated, sized, and then added in the form of dry granules or a dry powder to an aqueous gelatin solution. Alternatively, the slurry of OCP may be concentrated by centrifugal sedimentation, then recovered, and added in the form of dry granules or a dry powder to an aqueous gelatin solution.

The heat-treatment is performed at 50° C. to 200° C., preferably 100° C. to 150° C., for 3 to 240 hours, and preferably 24 to 100 hours. The OCP to be mixed with gelatin (hereinafter also referred to as C-OCP) is thereby prepared. It has become clear that heating under these conditions does not affect the crystal structure of OCP particles or physical properties of the surface of OCP particles (including the particle size) (Suzuki O, et al., Bone Miner 1993; 20: 151-166).

The OCP after drying may optionally be sized to granules with an appropriate particle size using a screening means such as a sieve, and the granules may be dispersed in an aqueous gelatin solution as described below to produce an OCP/Gel complex. The lower limit of the OCP particle size after sizing is not particularly limited and may be appropriately selected, for example, from 10 μm, 20 μm, 30 μm, 40 μm, 50 μm, 53 μm, 100 μm, 200 μm, 295 μm, 300 μm, 400 μm, and the like. The upper limit of the particle size after sizing is not particularly limited and may be appropriately selected, for example, from 900 μm, 800 μm, 700 μm, 600 μm, 500 μm, 400 μm, 300 μm, 295 μm, and the like. The particle size range after sizing is not particularly limited and may be appropriately selected, for example, from the range of 10 to 500 μm, 50 to 300 μm, 53 to 300 μm, 300 to 500 μm, or the like. The gelatin concentration of the aqueous gelatin solution is not particularly limited, and is preferably 0.1 to 5% (w/v), and more preferably 0.5 to 4% (w/v). When OCP is mixed with an aqueous solution containing gelatin in a relatively high concentration, such as 1 to 5% (w/v), and preferably 2 to 4% (w/v), the obtained material is expected to have another advantage of being easy to handle.

2. Preparation of OCP by a Wet Method

In another aspect of the method of the present invention, OCP is produced by using a wet method. OCP may be a commercially available product or may be synthesized, for example, by a known wet method (Suzuki O et al., Tohoku J Exp Med 1991; 164: 37-50). Alternatively, a nonstoichiometric OCP (low crystalline OCP: Japanese Patent Application No. 2008-284109), which is obtained by partially hydrolyzing OCP produced by using a known wetting method, may also be used.

The obtained OCP may be dried at a temperature of 50° C. to 200° C., and preferably 100° C. to 150° C., for 3 to 240 hours, preferably 24 to 100 hours. OCP is usually a precipitate of aggregated crystals. OCP is usually sized to granules having a particle size of about 10 to 1,000 µm and used.

Next, OCP may optionally be further sized to an appropriate particle size using a screening means such as a sieve. The lower limit of the OCP particle size after sizing is not particularly limited and may be appropriately selected, for example, from 10 µm, 20 µm, 30 µm, 40 µm, 50 µm, 53 µm, 100 µm, 200 µm, 295 µm, 300 µm, 400 µm, and the like. The upper limit of the particle size after sizing is not particularly limited and may be appropriately selected, for example, from 900 µm, 800 µm, 700 µm, 600 µm, 500 µm, 400 µm, 300 µm, 295 µm, and the like. The particle size range after sizing is not particularly limited and may be appropriately selected, for example, from the range of 10 to 500 µm, 50 to 300 µm, 53 to 300 µm, 300 to 500 µm, and the like. The OCP to be mixed with gelatin (also referred to as W-OCP) is thereby prepared. The sized W-OCP may be mixed with gelatin directly or after a small amount of water is added to form an OCP/Gel complex.

Although OCP in an OCP/Gel complex can be assumed to have substantially the same dimensions as OCP formed into a complex by dispersing OCP in an aqueous gelatin solution and freeze-drying, the particle size of OCP in the OCP/Gel complex can be confirmed by SEM, etc.

As long as the effect of the present invention is achieved, a complex further containing a trace amount of OCP having a particle size outside the above-mentioned particle size range is also included within the scope of the present invention.

3. Production of an OCP/Gel Complex from the Prepared OCP

Next, C-OCP obtained in "1. Preparation of OCP by using a co-precipitation method" or W-OCP obtained in "2. Preparation of OCP by using a wet method" is dispersed in an aqueous gelatin solution. The concentration of gelatin in the aqueous gelatin solution is not particularly limited and is preferably 0.1 to 5% (w/v), and more preferably 0.5 to 4% (w/v). The pH of the aqueous gelatin solution is not particularly limited and is preferably 5 to 8. The aqueous gelatin solution may contain a buffer component, phosphate ions, and calcium ions. The proportion of OCP to be dispersed in an aqueous gelatin solution relative to gelatin is not particularly limited and is usually 0.1 to 9 parts by mass, preferably 0.6 to 9 parts by mass, per part by mass of gelatin.

The OCP/Gel complex usually contains OCP in an amount of 10 mass % to 90 mass % and gelatin in an amount of 10 mass % to 90 mass %, based on the mass of the complex. Preferably, the OCP/Gel complex contains OCP in an amount of 20 mass % to 90 mass % and gelatin in an amount of 10 mass % to 80 mass %, based on the mass of the complex. More preferably, the OCP/Gel complex contains OCP in a high concentration, i.e., in an amount of 40 mass % to 90 mass %, and gelatin in an amount of 10 to 60 mass %, based on the mass of the complex. The complex may contain a third component as described herein below.

The total amount of OCP and gelatin in the OCP/Gel complex, which is a bone regeneration material of the present invention, is 60 mass % or more, preferably 80 mass % or more, more preferably 90 mass % or more, even more preferably 95 mass % or more, still even more preferably 98 mass % or more, and most preferably 99 mass % or more, based on the mass of the OCP/Gel complex, i.e., when the mass of the OCP/Gel complex is defined as 100 mass %. In a preferable embodiment, the OCP/Gel complex consists of OCP and Gel and does not substantially contain any other component.

In one embodiment, the OCP/Gel complex contains OCP in an amount of 10 mass % to 90 mass %, and the proportion of octacalcium phosphate to gelatin is 0.6 to 9 parts by mass of OCP per part by mass of gelatin. In another embodiment, the OCP/Gel complex contains OCP in an amount of 10 mass % to 90 mass % and gelatin in an amount of 10 to 90 mass %. In another embodiment, the OCP/Gel complex contains OCP in an amount of 20 mass % to 90 mass %, and the proportion of octacalcium phosphate to gelatin is 0.6 to 9 parts by mass of OCP per part by mass of gelatin. In another embodiment, the OCP/Gel complex contains OCP in an amount of 20 mass % to 90 mass %, and the proportion of octacalcium phosphate to gelatin is 0.6 to 9 parts by mass per part by mass of gelatin. In another embodiment, the OCP/Gel complex contains OCP in an amount of 20 mass % to 90 mass % and gelatin in an amount of 10 mass % to 80 mass %. In another embodiment, the OCP/Gel complex contains OCP in an amount of 40 mass % to 90 mass % and the proportion of octacalcium phosphate to gelatin is 0.6 to 9 parts by mass of OCP per part by mass of gelatin. In another embodiment, the OCP/Gel complex contains OCP in an amount of 40 mass % to 90 mass % and gelatin in an amount of 10 mass % to 60 mass %. In another embodiment, the OCP/Gel complex contains OCP in an amount of more than 40 mass % but not more than 90 mass %, and the proportion of octacalcium phosphate to gelatin is 0.6 to 9 parts by mass of OCP per mass by mass of gelatin. In another embodiment, the OCP/Gel complex contains OCP in an amount of more than 40 mass % but not more than 90 mass % and gelatin in an amount of at least 10 mass % and less than 60%. In another embodiment, the OCP/Gel complex contains OCP in an amount of more than 40 mass % but not more than 90 mass %, and the proportion of octacalcium phosphate to gelatin is 0.6 to 9 parts by mass of OCP per part by mass of gelatin. In another embodiment, the OCP/Gel complex contains OCP in an amount of more than 40 mass % but not more than 90 mass % and gelatin in an amount of at least 10 mass % and less than 60 mass %. The particle size of OCP obtained by the wet method according to these embodiments is in the range of 10 to 1,000 µm, such as 300 to 500 µm.

When using the OCP/Gel complex according to the above embodiments, a bone with a good bone quality can be generated.

When OCP is prepared by using a co-precipitation method, gelatin is once removed from an OCP/Gel complex and then OCP is mixed with an aqueous gelatin solution again. This facilitates the adjustment of the proportions of OCP and gelatin and enables the production of an OCP/Gel complex containing OCP in a concentration of more than 40 mass %, which has been difficult to produce heretofore. When OCP is prepared by using a wet method, a complex can be produced even when the concentration of the aqueous gelatin solution is high, i.e., an OCP/gelatin complex can be produced even when the aqueous gelatin solution has a high gelatin concentration, and the obtained complex is easy to handle. The OCP/Gel complex obtained by using a wet method has a relatively high elastic modulus even when the complex contains OCP in a low concentration. The elastic modulus may be, for example, 0.4 MPa or more. In one embodiment, when the OCP/Gel complex contains OCP in an amount of less than 50 mass %, the OCP/Gel complex has an elastic modulus of more than 0.3 MPa; when the OCP/Gel complex contains OCP in an amount of 50 mass % or more, the OCP has an elastic modulus of more than 0.4 MPa.

Next, the dispersion of OCP dispersed in the aqueous gelatin solution is dried to obtain an OCP/Gel complex. The drying is usually freeze-drying, and the drying conditions are not particularly limited. The pre-freezing temperature may be, for example, −10 to −196° C. The freezing temperature may be, for example, −40 to −90° C. The pressure may be, for example, 50 Pa or less. The freeze-dried product is usually obtained in 10 to 72 hours. This freeze-dried product is one embodiment of the OCP/Gel complex.

The freeze-dried product may be further subjected to a thermal crosslinking treatment. The thermal crosslinking treatment can enhance the stability of the OCP/Gel complex. The thermal crosslinking conditions are not particularly limited. The thermal crosslinking treatment temperature may be, for example, 100 to 200° C., and the treatment time is usually 6 to 48 hours.

The bone regeneration material comprising the OCP/Gel complex of the present invention may contain any component generally incorporated in bone regeneration materials as long as the component does not impair the effect of the invention. Examples of such components include bioabsorbable polymers (e.g., polylactic acids and polylactic acid-polyethylene glycol copolymers), bioabsorbable calcium phosphate (e.g., β-TCP), and non-bioabsorbable materials (e.g., HA ceramics).

The bone regeneration material of the present invention usually has a pore size of 10 to 500 μm, and preferably 100 to 300 μm. When the pore size is more than 10 μm, infiltration of cells into pores is smooth. When the pore size is 500 μm or less, the strength of the bone regeneration material is maintained. The bone regeneration material usually has an elastic modulus of 0.1 to 1.0 MPa, and preferably 0.2 to 0.6 MPa. When the elastic modulus is 0.1 MPa or more, the hardness of the bone regeneration material is maintained and a molded article composed of the bone regeneration material is thus easy to handle. When the bone regeneration material has an elastic modulus of 1.0 MPa or less, a molded article composed of the bone regeneration material can be easily processed into the shape of a bone defect.

The bone regeneration material of the present invention is appropriately molded and used. The molding means is not particularly limited. Examples of molding means include a method comprising placing a bone regeneration material in an appropriate mold and hardening the material, a method comprising hardening a bone regeneration material while applying pressure. The shape of the molded article is not particularly limited and may be, for example, a disk, a block, or a sheet. The size of the disk is not particularly limited. For example, the diameter of the disk is usually 3 to 20 mm, and preferably 5 to 10 mm. For example, the thickness of the disk is usually 0.5 to 5 mm, and preferably 1 to 2 mm. The size of the block is not particularly limited. For example, the block may have a length of 5 to 15 mm, a width of 5 to 50 mm, and a height of 5 to 100 mm, and preferably a length of 8 to 12 mm, a width of 10 to 30 mm, and a height of 10 to 50 mm.

The molded article is appropriately shaped according to the configuration of a bone defect and implanted into the bone defect after being subjected to a sterilization treatment, such as radiation sterilization or autoclave sterilization. However, when autoclave sterilization is used, the sites of bone defects to be created should be considered because autoclave sterilization affects the crystal phase of OCP.

The disclosures of all patent applications and publications referred to herein are incorporated herein by reference in their entirety.

The present invention is more specifically described below with reference to Examples. However, the scope of the invention is not limited to these Examples.

EXAMPLES

Example 1

Preparation of OCP (C-OCP) by a Co-Precipitation Method

In the presence of a solution containing gelatin in a final concentration of 0.5% (w/v) (a porcine skin-derived gelatin dry powder (produced by Sigma-Aldrich, St. Louis, Mo.)) dissolved in pure water to a final concentration of 0.5% (w/v)), an OCP/Gel slurry was synthesized using a solution containing calcium (calcium acetate monohydrate, final molar concentration: 0.040 mol/L) and phosphoric acid (sodium dihydrogen phosphate dihydrate, final molar concentration: 0.040 mol/L) by a co-precipitation method (Handa T et al., Acta Biomater 2012; 8: 1190-1200). The obtained slurry was washed with pure water 5 times to remove gelatin, thus obtaining an OCP slurry. A specific amount of the OCP slurry was sampled. After the slurry was dried at 105° C. for 24 hours, the mass was measured to calculate the OCP content per mL of the slurry.

Preparation of OCP (W-OCP) by the Wet Method

OCP granules were synthesized in a usual manner by a wet method (Suzuki O et al., Tohoku J Exp Med 1991; 164: 37-50) and dried at 105° C. for 24 hours. After drying, the OCP granules were sized to a particle size of 300 to 500 μm using a sieve. In order to produce final OCP/Gel complexes containing OCP in concentrations of 17, 29, and 44 mass %, the sized W-OCP was weighed and added to a small amount of pure water to produce each of the W-OCP suspensions.
Production of OCP/Gel Disk
(1) Preparation of Gelatin Solutions A porcine skin-derived gelatin dry powder (produced by Sigma-Aldrich, St. Louis, Mo.) was added to pure water to final concentrations of 0.5% (w/v) and 3.0% (w/v), stirred at room temperature for 30 minutes, and swollen. In this process, pure water was weighed to produce the amount calculated by subtracting the volume of the C-OCP slurry or W-OCP suspension to be added later from the amount of the final OCP/Gel solution. After swelling and dissolution, the solution was heated while stirring at a solution temperature of 40 to 50° C. to completely dissolve the gelatin.

(2) Addition of OCP and Formation of Disks

The C-OCP slurry or the W-OCP suspension was added to and mixed with one of the gelatin solutions obtained in (1) to produce OCP/Gel complexes containing OCP in concentrations of 17, 29, and 44%. The C-OCP slurry was mixed with the 0.5% (w/v) aqueous gelatin solution, and the W-OCP suspension was mixed with the 3.0% (w/v) aqueous gelatin solution. The mixture of the C-OCP slurry with the 0.5% (w/v) aqueous gelatin solution or the mixture of the W-OCP suspension with the 3.0% (w/v) aqueous gelatin solution was placed into a resin tube with an inner diameter of 9 mm, pre-frozen at −20° C. for 24 hours, and then freeze-dried for 3 days to produce a cylindrical OCP/Gel complex. After the cylindrical OCP/Gel complex was cut and shaped into a disk (9 mm in diameter and 1 mm in thickness), the disk was subjected to thermal crosslinking treatment (150° C., for 24 hours) using a vacuum dryer (Vacuum Drying Oven DP32, produced by Yamato Scientific Co., Ltd.) and sterilized. The OCP/Gel disks thus obtained contained OCP and gelatin in the following proportions: when the proportions of OCP were 17, 29, and 44 mass %, the proportions of gelatin were 83, 71, and 56 mass %, respectively.

Example 2

Assessment (1) Investigation of Bone Formation

Wistar, 12-week-old, male rats were placed under general anesthesia using sevoflurane and medetomidine hydrochloride, midazolam, and butorphanol. Subsequently, the cranial skin of the rats was shaved and the exposed skin and the underlying periosteum were cut with a scalpel. A bone defect having a diameter of 9 mm was created in the skull midline. Subsequently, each OCP/Gel disk obtained in Example 1 was implanted into each bone defect, and the periosteum and skin were sutured.

Figure 2:
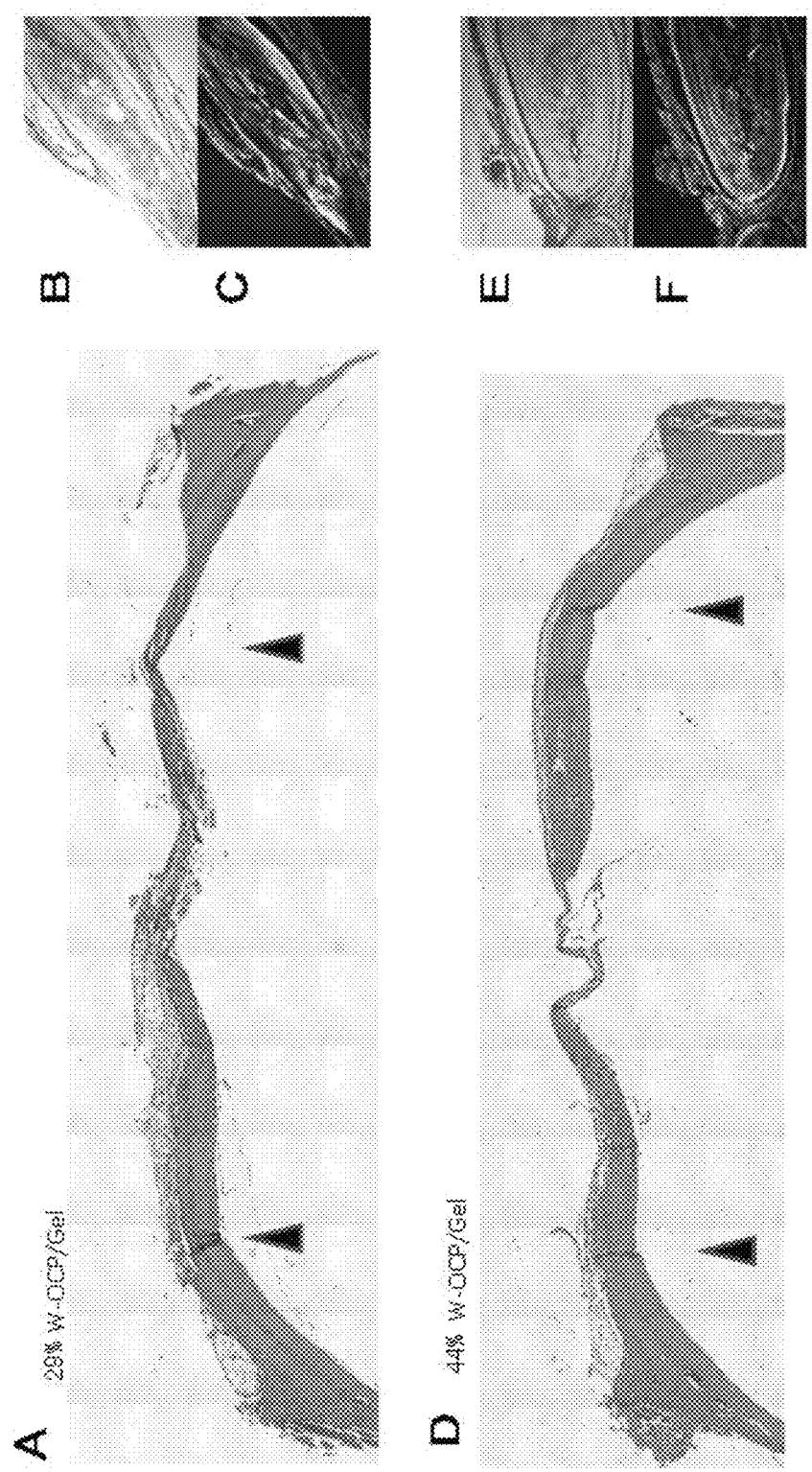
FIG. 2 shows photographs (A, D) of hematoxylin and eosin staining showing the cross sections of regenerated skulls in rats 8 weeks after each OCP/Gel disk produced by a wet method was implanted into a bone defect in the skull (wherein black triangles indicate the sites of defects created); bright-field photographs (B, E) of Sirius red staining; and polarized light photographs (C, F); A to C: OCP/Gel (29/71) disks and D to F: OCP/Gel (44/56) disks.

Eight weeks after the implantation, decalcified specimens of skulls removed from the rats were histologically analyzed by hematoxylin and eosin (HE) staining and Sirius red staining. The specimens stained with Sirius red were observed using bright-field microscopy and polarized light microscopy. FIG. 1 shows the results obtained using the OCP/Gel disks produced by the co-precipitation method. FIG. 2 shows the results obtained using the OCP/Gel disks produced by the wet method.

FIG. 1 shows that when materials containing OCP in concentrations of 17 mass % to 44 mass % were investigated by using OCP/Gel disks (C-OCP/Gel) produced using OCP prepared by the co-precipitation method and using as gelatin a solution containing gelatin in an initial concentration of 0.5% (w/v) and the OCP/Gel disks were implanted into calvarial bone defects in the rats and investigated 8 weeks after the implantation, regeneration of well-ordered bone with good bone formation capacity and good absorption of materials was confirmed. Specifically, photographs of hematoxylin and eosin (HE) staining (FIGS. 1A, D, and G) show that the sites of defects created (black triangles) into which OCP/Gel disks containing OCP in concentrations of 17 mass %, 29 mass %, and 44 mass % were implanted were all repaired well, compared with the controls into which no OCP/Gel complexes were implanted (not shown). Further, bright-field photographs of Sirius red staining (FIGS. 1B, E, and H) show that the regenerated bone matrix (collagen) became closer to the maternal bed bone (on the lower side of the photograph), and regeneration of well-ordered bone was confirmed. Polarized light photographs of Sirius red staining (FIGS. 1C, F, and I) prominently show the contrast of the running of collagen fibers in bright-field photographs, and confirm that as the OCP concentration increases, the regenerated bone has a better bone quality.

FIG. 2 shows that when materials containing OCP in concentrations of 29 mass % and 44 mass % were investigated by using OCP/Gel disks (W-OCP/Gel) produced using OCP prepared by the wet method, regeneration of well-ordered bone with good bone formation capacity and good absorption of materials was confirmed as in the results, shown in FIG. 1, of the OCP/Gel disks produced using the co-precipitation method. Specifically, photographs of hematoxylin and eosin (HE) staining (FIGS. 2A and D) show that the sites of defects created (black triangles) into which OCP/Gel disks containing OCP in concentrations of 29 mass % and 44 mass % were implanted were both repaired well, compared with the controls into which no OCP/Gel complexes were implanted (not shown). Further, photographs of Sirius red staining (FIGS. 2B and E) show that the regenerated bone matrix (collagen) became closer to the maternal bed bone (on the lower side of the photograph), and regeneration of well-ordered bone was confirmed.

Polarized light photographs (FIGS. 2C and F) prominently show the contrast of the running of collagen fibers in Sirius red staining photographs. The photographs confirm that as the OCP concentration increases, the regenerated bone has a better bone quality.

(2) Determination of Percentage of Bone Formation by Staining

The amount of bone formation and the residual OCP amount of each OCP/Gel disk (C-OCP/Gel) produced using OCP prepared by the co-precipitation method were determined by histomorphometry from the results of HE staining. The percentage of the bone formation was calculated according to the following formula:

Percentage of new bone formation=Amount of bone formation/Bone defect area×100

Table 1 shows that when C-OCP/Gel disks produced by the co-precipitation method were implanted into rats, significantly high percentages of bone formation were achieved after 8 weeks and 12 weeks, compared to those in the controls (p<0.01), and that a high percentage of formation of more than 50% was achieved whether the OCP/Gel disk implanted had an OCP concentration of 17 mass %, 29 mass %, or 44 mass %. The results further show that as the OCP concentration increases, the percentage of the bone formation tends to increase (average value±standard deviation, n=5 per group, however, the number of rats in the 8-week control group and 17% C-OCP/Gel group was n=4, the results after 8 weeks: control: 14.05±9.09%, 17% C-OCP/Gel: 65.79±6.16%, 29% C-OCP/Gel: 59.16±15.00%, 44% C-OCP/Gel: 74.76±9.68%; the results after 12 weeks: control: 30.17±4.90, 17% C-OCP/Gel: 62.71±9.97%, 29% C-OCP/Gel: 79.73±4.28%, 44% C-OCP/Gel: 80.56±8.03%).

TABLE 1

| | New bone/Bone defect region (%) | | | | | | | |
|---|---|---|---|---|---|---|---|---|
| | Control | | 17% C-OCP/Gel | | 29% C-OCP/Gel | | 44% C-OCP/Gel | |
| | 8 W | 12 W | 8 W | 12 W | 8 W | 12 W | 8 W | 12 W |
| Average | 14.0 | 30.2 | 65.8 | 62.7 | 59.2 | 79.7 | 74.8 | 80.6 |
| SD | 9.1 | 4.9 | 6.2 | 10.0 | 15.0 | 4.3 | 9.7 | 8.0 |

Further, from the results of Sirius red staining, the percentage of highly oriented bone formation in the new bone was calculated. First, the new bone area was measured from a bright-field image. Next, the highly oriented new bone area (area of highly oriented collagen fibers appearing green-blue in color under polarized light) was measured from a polarized image of the same specimen. The percentage of highly oriented bone formation was calculated according to the following formula:

Percentage of highly oriented bone formation=Highly oriented new bone area/New bone area×100

(n in each group is the same as in HE staining).

Table 2 shows that when C-OCP/Gel disks produced by the co-precipitation method were implanted into rats, the percentages of highly oriented bone formation in the new bone after 8 weeks and 12 weeks were significantly higher than those in the controls ($p<0.05$), whether the OCP/Gel disks implanted had OCP concentration of 17 mass %, 29 mass %, or 44 mass %. The results further show that as the OCP concentration increase, the percentage of highly oriented bone formation also tends to increase (average value±standard deviation, n=5 per group, however, the number of rats in the 8-week control group and 17% C-OCP/Gel group was n=4, the results after 8 weeks: control: 0.63±0.48%, 17% C-OCP/Gel: 33.25±6.34%, 29% C-OCP/Gel: 41.78±9.83%, 44% C-OCP/Gel: 50.00±4.69%; the results after 12 weeks: control: 0.93±1.41, 17% C-OCP/Gel: 47.58±12.13%, 29% C-OCP/Gel: 66.25±9.91%, 44% C-OCP/Gel: 68.00±8.08%).

TABLE 2

| | Highly oriented bone/Bone (%) | | | | | | | |
|---|---|---|---|---|---|---|---|---|
| | Control | | 17% C-OCP/Gel | | 29% C-OCP/Gel | | 44% C-OCP/Gel | |
| | 8 W | 12 W | 8 W | 12 W | 8 W | 12 W | 8 W | 12 W |
| Average | 0.6 | 0.9 | 33.3 | 47.6 | 41.8 | 66.3 | 50.0 | 68.0 |
| SD | 0.5 | 1.4 | 6.3 | 12.1 | 9.8 | 9.9 | 4.7 | 8.1 |

(4) Elastic Modulus

The elastic modulus of each of the OCP/Gel disks obtained in Example 1 was measured using a universal tester (EZ-L-500N, produced by Shimadzu Corp.). Each disk having an inner diameter of 9 mm×a thickness of 1 mm was placed in a jig for compression tests, and a load-displacement curve was obtained at a constant crosshead speed. Stress-strain values (stress/strain:elastic modulus) were calculated from load-displacement values in a continuously curved portion. Table 3 shows the results.

Table 3 clearly shows that when using the OCP/Gel disks (W-OCP/Gel) produced using OCP prepared by the wet method, the elastic modulus increases as the proportion of OCP increases, and the OCP/Gel disks had such an elastic modulus as to be easily handled upon implantation (n=4 per group, 29% W-OCP/Gel: 0.38±0.04 MPa, 44% W-OCP/Gel: 0.49±0.03 MPa.) These elastic modulus values of the OCP/Gel disks (W-OCP/Gel) were higher than those of OCP/Gel disks (C-OCP/Gel) produced using OCP prepared by the co-precipitation method (n=4 per group, 17% C-OCP/Gel: 0.014±0.001 MPa, 29% C-OCP/Gel: 0.012±0 MPa, 44% C-OCP/Gel: 0.018±0.004 MPa).

TABLE 3

| | Elastic modulus (MPa) | | | | |
|---|---|---|---|---|---|
| | 17% C-OCP/ 0.5% Gel | 29% C-OCP/ 0.5% Gel | 44% C-OCP/ 0.5% Gel | 29% W-OCP/ 3.0% Gel | 44% W-OCP/ 3.0% Gel |
| Average | 0.014 | 0.012 | 0.018 | 0.377 | 0.489 |
| SD | 0.002 | 0.000 | 0.004 | 0.041 | 0.035 |

Further, a C-OCP/Gel complex and W-OCP/Gel complex were prepared in accordance with the procedures of Example 1. Specifically, C-OCP granules (particle size: 300 to 500 μm) were dispersed in 3% (w/v) gel to obtain a C-OCP/Gel complex containing OCP at a mass ratio of 77%. W-OCP granules (particle size: 300 to 500 μm) were dispersed in 3% (w/v) gel to obtain a W-OCP/Gel complex containing OCP at a mass ratio of 77%. The C-OCP/Gel complex containing OCP at a mass ratio of 77% had a significantly higher elastic modulus than C-OCP/Gel complexes containing OCP at a mass ratio of 17, 29, or 44 mass %, and the W-OCP/Gel complex containing OCP at a mass ratio of 77% had a significantly higher elastic modulus than W-OCP/Gel complexes containing OCP at a mass ratio of 17, 29, or 44 mass % (data not shown).

The invention claimed is:

1. A method for producing a bone regeneration material comprising a complex of octacalcium phosphate and gelatin, the method comprising:
   co-precipitating octacalcium phosphate with gelatin to produce a co-precipitate of octacalcium phosphate and gelatin;
   washing the co-precipitate with a washing liquid to remove gelatin from the co-precipitate, thus forming a slurry of octacalcium phosphate;

dispersing either the slurry of octacalcium phosphate or dry granules formed using the slurry in an aqueous gelatin solution; and drying the dispersion of octacalcium phosphate dispersed in the aqueous gelatin solution to produce a complex of octacalcium phosphate and gelatin.

2. The method according to claim 1, wherein the complex of octacalcium phosphate and gelatin contains octacalcium phosphate in an amount of more than 40 mass % but not more than 90 mass % and gelatin in an amount of 10 mass % or more and less than 60 mass %, based on the mass of the complex.

3. The method according to claim 1, wherein the complex of octacalcium phosphate and gelatin contains octacalcium phosphate in an amount of 10 mass % to 90 mass %, based on the mass of the complex.

4. A method for producing a bone regeneration material comprising a complex of octacalcium phosphate and gelatin, the method comprising:

dispersing octacalcium phosphate granules with a particle size of 10 to 1,000 μm in an aqueous gelatin solution; and drying the dispersion of octacalcium phosphate granules dispersed in the aqueous gelatin solution to produce a complex of octacalcium phosphate and gelatin, wherein the complex contains octacalcium phosphate in an amount of 10 mass % to 90 mass %, based on the mass of the complex, and the proportion of octacalcium phosphate to gelatin is 0.1 to 9 parts by mass of octacalcium phosphate per part by mass of gelatin.

5. The method according to claim 4, wherein octacalcium phosphate granules to be dispersed in the aqueous gelatin solution have a particle size of 300 to 500 μm.

6. The method according to claim 4, wherein the complex has an elastic modulus of 0.4 MPa or more.

7. The method according to claim 4, wherein the complex contains octacalcium phosphate in an amount of 20 mass % to 90 mass %, based on the mass of the complex, and the octacalcium phosphate in the complex has a particle size of 300 to 500 μm.

8. The method according to claim 5, wherein the complex has an elastic modulus of 0.4 MPa or more.

* * * * *